United States Patent
Mantri

(10) Patent No.: US 9,757,247 B2
(45) Date of Patent: Sep. 12, 2017

(54) INTERBODY FUSION IMPLANT

(71) Applicant: DePuy Synthes Products, Inc., Raynham, MA (US)

(72) Inventor: Kaustubh Mantri, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 237 days.

(21) Appl. No.: 13/653,715

(22) Filed: Oct. 17, 2012

(65) Prior Publication Data
US 2014/0094919 A1 Apr. 3, 2014

Related U.S. Application Data

(60) Provisional application No. 61/708,247, filed on Oct. 1, 2012.

(51) Int. Cl.
| | | |
|---|---|---|
| *A61F 2/44* | (2006.01) | |
| *A61F 2/30* | (2006.01) | |
| *A61F 2/28* | (2006.01) | |

(52) U.S. Cl.
CPC ............ *A61F 2/4425* (2013.01); *A61F 2/442* (2013.01); *A61F 2/447* (2013.01); *A61F 2002/2835* (2013.01); *A61F 2002/304* (2013.01); *A61F 2002/3008* (2013.01); *A61F 2002/30014* (2013.01); *A61F 2002/3027* (2013.01); *A61F 2002/30215* (2013.01); *A61F 2002/30324* (2013.01); *A61F 2002/30331* (2013.01); *A61F 2002/30354* (2013.01); *A61F 2002/30372* (2013.01); *A61F 2002/30373* (2013.01);
(Continued)

(58) Field of Classification Search
CPC .............................................. A61F 2/44–2/447
USPC .......................................... 623/17.11–17.16
See application file for complete search history.

(56) References Cited

U.S. PATENT DOCUMENTS 4,309,777 A * 1/1982 Patil ........................ A61F 2/442
606/247
5,676,702 A * 10/1997 Ratron ....................... 623/17.16
(Continued)

FOREIGN PATENT DOCUMENTS

| WO | WO 2005/092250 | 10/2005 |
| WO | WO 2007/075411 | 7/2007 |
| WO | WO 2010/141910 A2 | 12/2010 |

OTHER PUBLICATIONS van Dijk, The Effect of Cage Stiffness on the Rate of Lumbar Interbody Fusion, Spine, vol. 27, No. 7, 2002, 682-688.

*Primary Examiner* — Jan Christopher Merene
*Assistant Examiner* — Steven Cotroneo
(74) *Attorney, Agent, or Firm* — Baker & Hostetler LLP

(57) ABSTRACT

An intervertebral implant can include a core and a flexible end plate. The core can have a core body that is elongate along a first direction and defines first and second outer surfaces. The flexible end plate can define an inner surface and an opposed bone facing surface that is configured to abut a vertebral body. The flexible end plate can be coupled to the core such that at least a portion of the inner surface faces the first outer surface and is spaced from the first outer surface. The flexible end plate is configured to resiliently flex toward a compressed configuration such that as the flexible end plate flexes toward the compressed configuration, a first end moves relative to the core along the first direction and the portion of the inner surface moves toward the first outer surface.

28 Claims, 7 Drawing Sheets

(52) U.S. Cl.
CPC ............ *A61F 2002/30397* (2013.01); *A61F 2002/30472* (2013.01); *A61F 2002/30492* (2013.01); *A61F 2002/30507* (2013.01); *A61F 2002/30563* (2013.01); *A61F 2002/30565* (2013.01); *A61F 2002/30566* (2013.01); *A61F 2002/30571* (2013.01); *A61F 2002/30598* (2013.01); *A61F 2002/30601* (2013.01); *A61F 2002/30611* (2013.01); *A61F 2002/30616* (2013.01); *A61F 2002/30777* (2013.01); *A61F 2002/30784* (2013.01); *A61F 2002/30785* (2013.01); *A61F 2002/30813* (2013.01); *A61F 2002/30836* (2013.01); *A61F 2002/4475* (2013.01); *A61F 2310/00023* (2013.01)

(56) References Cited

U.S. PATENT DOCUMENTS

| | | | |
|---|---|---|---|
| 6,395,035 B2 | 5/2002 | Bresina et al. | |
| 6,419,705 B1* | 7/2002 | Erickson | 623/17.16 |
| 6,830,589 B2* | 12/2004 | Erickson | 623/17.15 |
| 7,122,055 B2 | 10/2006 | Ralph et al. | |
| 7,141,070 B2* | 11/2006 | Ralph et al. | 623/17.13 |
| 7,214,244 B2 | 5/2007 | Zubok et al. | |
| 7,871,441 B2* | 1/2011 | Eckman | 623/17.11 |
| 8,016,886 B2 | 9/2011 | Albert et al. | |
| 8,070,814 B2 | 12/2011 | Zubok et al. | |
| 8,518,120 B2* | 8/2013 | Glerum et al. | 623/17.16 |
| 8,597,360 B2* | 12/2013 | McLuen | A61F 2/4455 623/17.16 |
| 2005/0096744 A1 | 5/2005 | Trieu et al. | |
| 2008/0071375 A1* | 3/2008 | Carver et al. | 623/17.13 |
| 2008/0154381 A1* | 6/2008 | Parrish | 623/17.16 |
| 2008/0167686 A1 | 7/2008 | Trieu et al. | |
| 2008/0177389 A1* | 7/2008 | Parrish | 623/17.16 |
| 2010/0004748 A1 | 1/2010 | Cordaro | |
| 2010/0016970 A1 | 1/2010 | Kapitan et al. | |
| 2011/0087333 A1 | 4/2011 | Kellar et al. | |
| 2011/0112644 A1 | 5/2011 | Zilberstein | |
| 2013/0304214 A1* | 11/2013 | Siegal et al. | 623/17.16 |

* cited by examiner

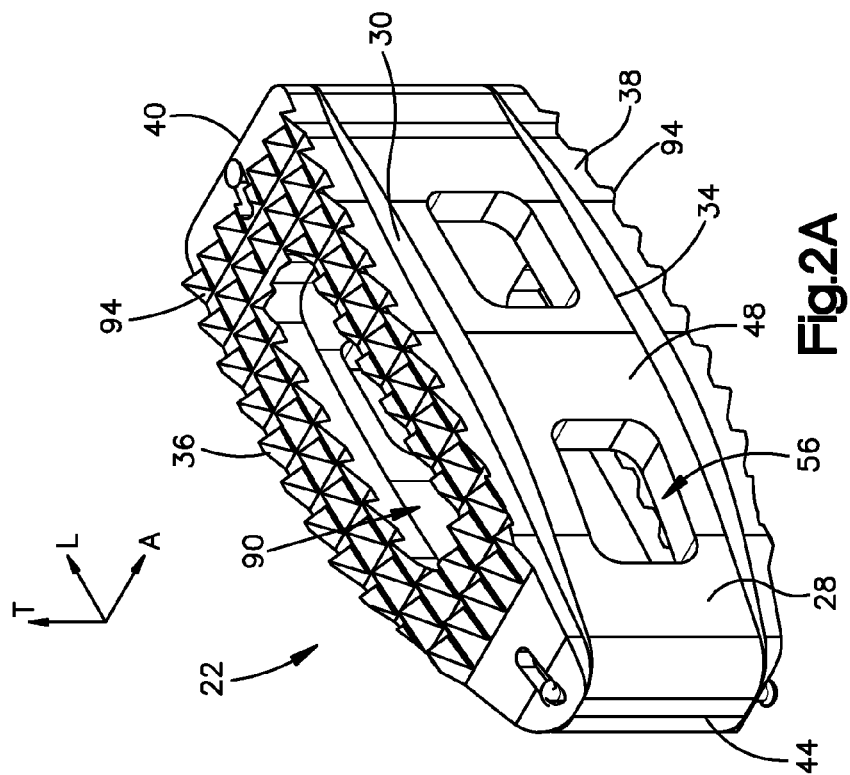
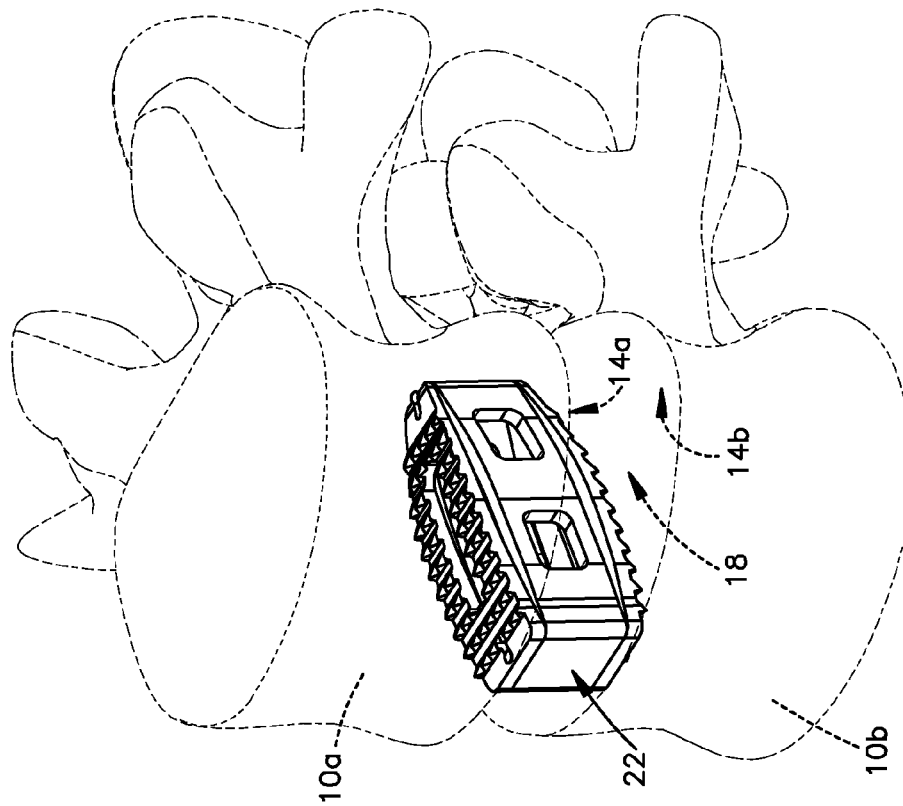

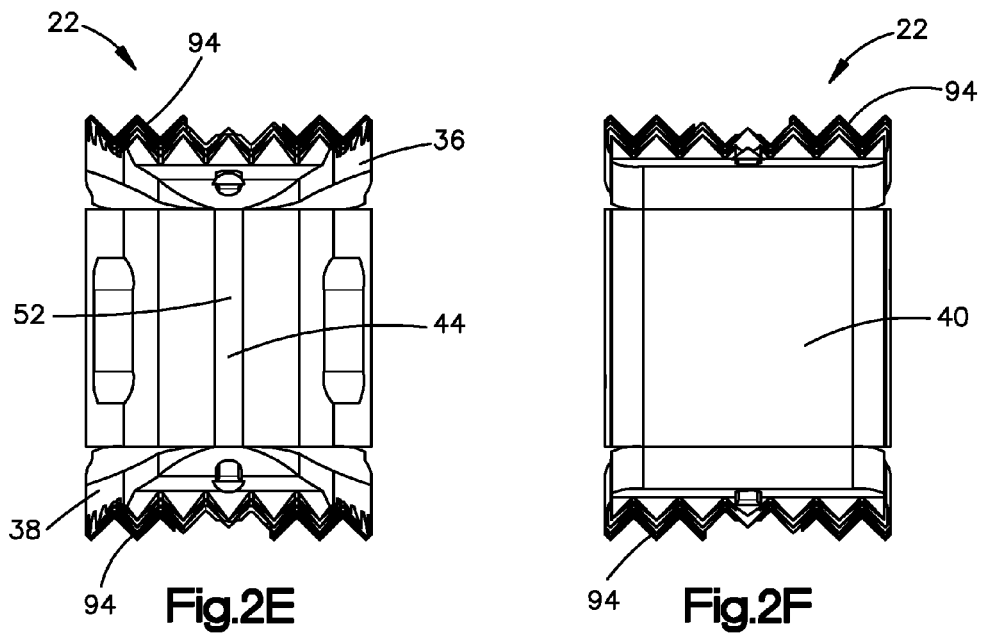
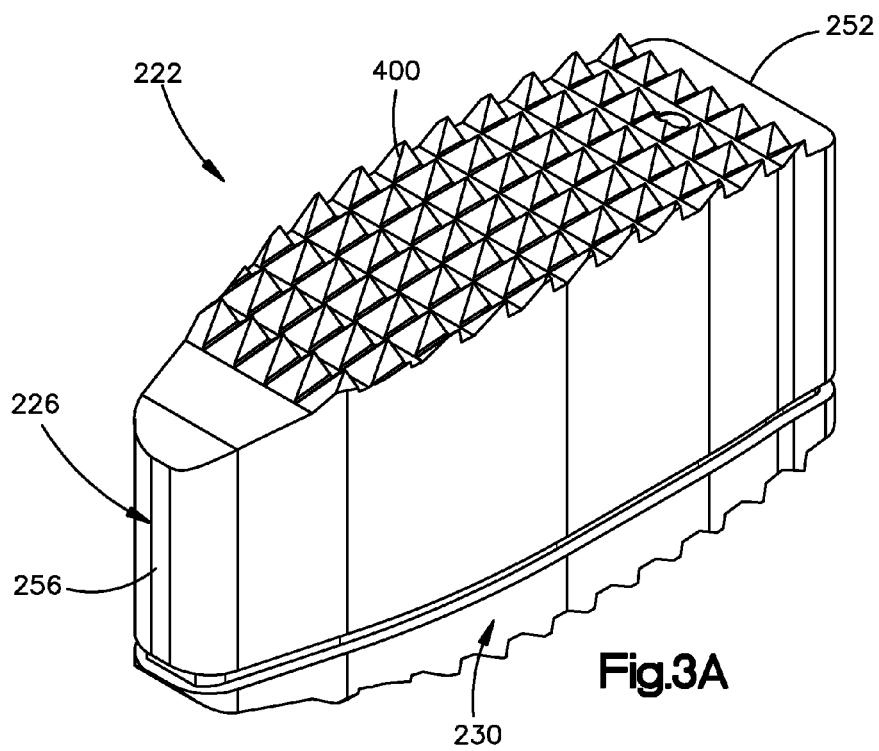

INTERBODY FUSION IMPLANT

CROSS-REFERENCE TO RELATED APPLICATION

This application claims priority to U.S. Provisional Application No. 61/708,247, filed Oct. 1, 2012, the contents of which are hereby incorporated by reference herein.

BACKGROUND

The placement of a fusion implant within an intervertebral space that is defined between adjacent vertebral bodies has typically resulted in the fusion of the adjacent vertebral bodies together. This "interbody fusion" procedure, which is in use today, is a widely accepted surgical treatment for symptomatic lumbar and cervical degenerative disc disease (DDD). The aim of a spinal fusion is to relieve pain caused by a degenerated disc, restore anatomy (disc height and/or lordotic curvature), and immobilize the affected level (fusion).

It has been found that the stiffness of the implants affects the rate of interbody fusion and that by reducing the stiffness of the implant the rate of interbody fusion can be increased.

SUMMARY

In an embodiment, an intervertebral implant can include a core and an end plate, the core can define a rear end and a front end that is spaced from the rear end along an insertion direction. The end plate can define a bone facing surface and an inner surface that is opposite the bone facing surface, the end plate further defining a first attachment member and a second attachment member that is spaced from the first attachment member, the first and second attachment members being movably coupled to the core such that at least a portion of the inner surface faces the core and is spaced from the core a first distance along a first direction that is substantially perpendicular to the insertion direction. The end plate is configured to resiliently move toward the core along the first direction such that 1) the portion of the inner surface is spaced from the core a second distance along the first direction that is less than the first distance, and 2) at least one of the first and second attachment members moves along the core.

In an embodiment, an intervertebral implant can include a core and a flexible end plate. The core can have a core body that is elongate along a first direction and defines first and second outer surfaces that are spaced from each other along a second direction that is perpendicular to the first direction. The flexible end plate can define an inner surface and an opposed bone facing surface that is configured to abut a vertebral body. The flexible end plate can be coupled to the core such that at least a portion of the inner surface faces the first outer surface and is spaced from the first outer surface by a distance. The flexible end plate can further define a first end and a second end that is spaced from the first end along the first direction. The flexible end plate is configured to resiliently flex toward a compressed configuration such that as the flexible end plate flexes toward the compressed configuration, the first end moves relative to the core along the first direction and the portion of the inner surface moves toward the first outer surface such that the distance is decreased.

In an another embodiment, an intervertebral implant can include a first end plate, a second end plate, and a biasing member coupled between the first and second endplates along a first direction. The first end plate can include a first body that defines a first bone facing surface and a first internal ceiling surface that is opposite the first bone facing surface along a first direction, the first end plate further including at least one wall that extends from the first body substantially along the direction, wherein the first end plate includes a cavity that is at least partially defined by the wall and the internal ceiling surface. The second end plate can include a second body that defines a second bone facing surface, the second body further defining a core having a second inner surface that is spaced from the second bone facing surface along the first direction, the core configured to be received in the cavity such that the second inner surface faces the internal ceiling surface. The first end plate is configured to move relative to the second end plate along the first direction between a first configuration and a second configuration whereby when in the first configuration the internal ceiling surface is spaced from the second inner surface along the first direction by a first distance, and when in the second configuration the internal ceiling surface is spaced from the second inner surface by a second distance that is less than the first distance, and movement of the first end plate from the first configuration to the second configuration causes the biasing member to compress so as to bias the first end plate along a direction from the second configuration toward the first configuration.

BRIEF DESCRIPTION OF THE DRAWINGS

The foregoing summary, as well as the following detailed description of illustrative embodiments of the interbody fusion implant of the present application, will be better understood when read in conjunction with the appended drawings. For the purposes of illustrating the intervertebral implant of the present application, there is shown in the drawings illustrative embodiments. It should be understood, however, that the application is not limited to the precise arrangements and implants shown. In the drawings:

FIG. 1 is a perspective view of an intervertebral implant positioned in an intervertebral space that is defined between a superior vertebral body and an inferior vertebral body;

FIG. 2A is a perspective view of an intervertebral implant in accordance with an embodiment, the implant including a core, a first flexible end plate coupled to a first surface of the core, and a second flexible end plate coupled to a second surface of the core;

FIG. 2E is a front elevation view of the intervertebral implant shown in FIG. 2A;

FIG. 2F is a rear elevation view of the intervertebral implant shown in FIG. 2A;

FIG. 3A is a perspective view of an intervertebral implant in accordance with another embodiment, the intervertebral implant including a first end plate that defines a cavity, a second end plate that defines a core, and a biasing member positioned within the first and second end plates such that as the first end plate moves relative to the second end plate from an initial configuration toward a compressed configuration, the biasing member biases the first end plate toward the initial configuration;

DETAILED DESCRIPTION

Figure 2B:
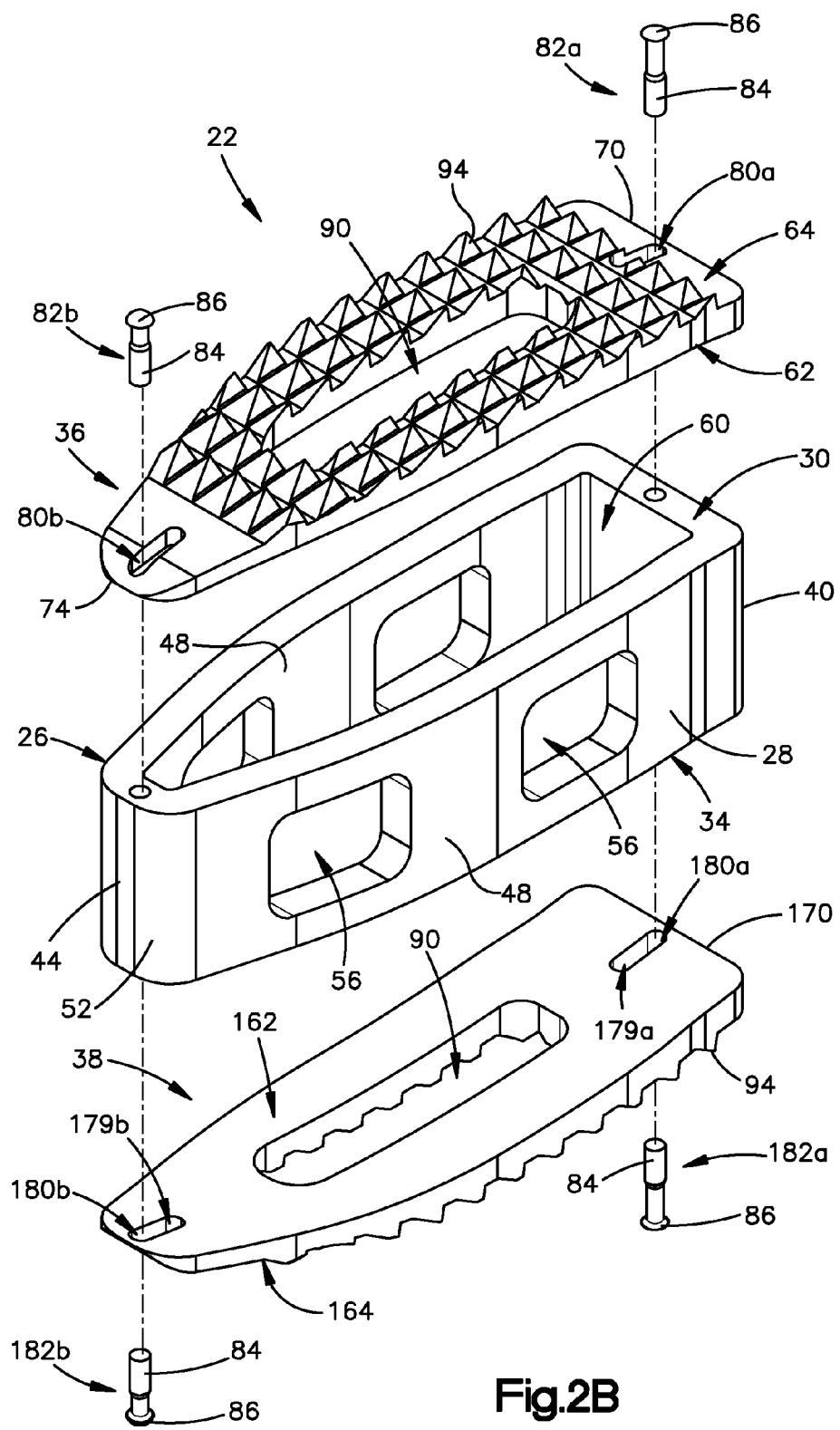
FIG. 2B is an exploded perspective view of the intervertebral implant shown in FIG. 2A.

Referring to FIG. 1, a superior vertebral body 10a defines a first or superior vertebral surface 14a of an intervertebral space 18, and an adjacent second or inferior vertebral body 10b defines an inferior vertebral surface 14b of the intervertebral space 18. Thus, the intervertebral space 18 is disposed between or otherwise defined by the vertebral bodies 10a and 10b. The intervertebral space 18 can be disposed anywhere along the spine as desired, including at the lumbar, thoracic, and cervical regions of the spine. As illustrated, the intervertebral space 18 is illustrated after a discectomy, whereby the disc material has been removed or at least partially removed to prepare the intervertebral space 18 to receive an intervertebral implant, such as intervertebral implant 22 that can achieve height restoration for example as shown in FIG. 1. The intervertebral implant can be configured as an interbody fusion implant and can be inserted into the intervertebral space 18 along an insertion direction such as from a posterior approach. It should be appreciated, however, that the intervertebral implant 22 can be inserted into the intervertebral space 18 along any insertion direction such as from an anterior approach.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

In Reference to FIGS. 2A-2F, the intervertebral implant 22 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the intervertebral implant 22 is implanted into the intervertebral space 18 along an insertion direction I, the transverse direction T extends vertically generally along the superior-inferior (or caudal-cranial) direction, while the horizontal plane defined by the longitudinal direction L and lateral direction A lies generally in the anatomical plane defined by the anterior-posterior direction, and the medial-lateral direction, respectively. Accordingly, the directional terms "vertical" and "horizontal" are used to describe the intervertebral implant 22 and its components as illustrated merely for the purposes of clarity and illustration.

As shown in FIGS. 2A and 2B, the intervertebral implant 22 can include a core 26 that has a core body 28 that is elongate along a first direction, such as along the longitudinal direction L or along the insertion direction, and defines a first or upper outer surface 30 and a second or lower outer surface 34 that is spaced from the first outer surface 30 along a second direction that is perpendicular to the first direction, such as along the transverse direction T. The intervertebral implant can further include a first flexible end plate 36 coupled to the first outer surface 30 of the core body 28, and a second flexible end plate 38 coupled to the second outer surface of the core body 28. Both the first flexible end plate 36 and the second flexible end plate 38 are configured to resiliently flex toward the core when the intervertebral implant 22 is inserted into the intervertebral space 18.

Figure 2C:
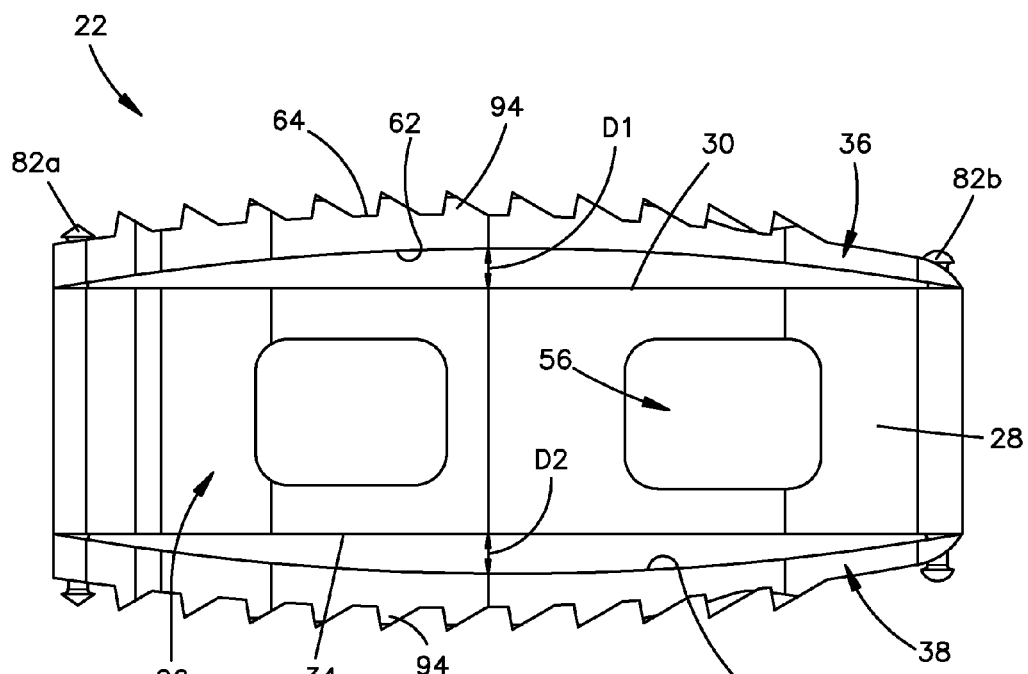
FIG. 2C is a side elevation view of the intervertebral implant shown in FIG. 2A.

As shown in FIGS. 2A-2C, the core body 28 can define a first or posterior or rear end 40 and a second or anterior or front end 44 and can include a pair of side walls 48 that extend from the posterior end 40 to the anterior end 44. The side walls 48 can be spaced from each other along a third direction, such as along the lateral direction A, such that the core 26 defines a cage. As shown, the side walls 48 extend toward each other as the side walls 48 extend from the posterior end 40 toward the anterior end 44 so as to define a nose 52 at the anterior end 44. The core 26 can be rigid and can be made from any suitable bio-compatible material such as metal or plastic. For example the core 26 can be made from PEEK or Titanium, as desired.

As shown in FIG. 2B, the core 26 can further include at least one window 56 that extends through the core body 28 along the third direction such as through the side walls 48 along the third direction. In the illustrated embodiment, the core 26 includes two windows 56 that extend through the core body 28. It should be appreciated, however, that the core 26 can include any number of windows 56 and can alternatively be void of windows 56 as desired. The windows 56 are configured to promote boney in-growth. As shown in FIG. 2B, the core 26 can also include at least one channel 60 that extends through the core body 28 along the second direction from the first outer surface 30 to the second outer surface 34. As with the windows 56, the channel 60 is configured to at least promote boney in-growth.

With continued reference to FIGS. 2A-2F, the first flexible end plate 36 defines an inner surface 62 and an opposed bone facing surface 64 that is configured to abut a vertebral body such as the vertebral body 10a when the intervertebral implant is disposed within the intervertebral space 18. As shown in FIG. 2C, the first flexible end plate 36 can be coupled to core 26 such that at least a portion of the inner surface 62 faces the first outer surface 30 and is spaced from the first outer surface 30 by a first distance $D_1$. The first distance $D_1$ can be a maximum distance that the inner surface 62 is spaced from the first outer surface 30 and can be taken at a longitudinal midline of the first flexible end plate 36 (e.g. halfway between first and second ends of the first flexible endplate 36). It should be appreciated, however, that the first distance $D_1$ can be taken at any point along the first flexible end plate 36.

As shown in FIGS. 2B and 2C, the first flexible end plate 36 can define a first or posterior end 70 and a second or anterior end 74 that is spaced from the first end 70 along the first direction. The first and second ends 70 and 74 can be coupled to the core body 28 such that the first flexible end plate 36 is bowed along the first direction. The flexible end plate 36 is flexible between a first or initial configuration and a second or compressed configuration such that as the end plate 36 flexes toward the compressed configuration the distance $D_1$ is decreased or the at least a portion of the inner surface 62 is spaced from the first outer surface 30 by a second distance that is less than the first distance $D_1$. That is, the first flexible end plate 36 is configured to resiliently flex toward the compressed configuration such that as the flexible end plate flexes toward the compressed configuration, the first end 70 moves along the core 26 or at least relative to the core 26 along the first direction and the portion of the inner surface 62 that faces the first outer surface 30 moves toward the first outer surface 30 such that the distance $D_1$ is decreased. Similarly, the second end 74 is configured to move along the core 26 or at least relative to the core 26 along the first direction and away from the first end 70 when the first flexible end plate 36 flexes toward the compressed configuration. When in the initial configuration the distance $D_1$ can be between about 0.5 mm and about 10.0 mm and when in the compressed configuration the second distance can be about 0.0 mm. It should be appreciated, however, that the first and second distances can be any number as desired when the first flexible end plate 36 is in the initial configuration or in the compressed configuration. Moreover, it should be appreciated, that while in the illustrated embodiment both the first and second ends 70 and 74 are configured to move along the first direction, in certain embodiments one of the first and second ends 70 and 74 can be fixed.

Figure 2D:
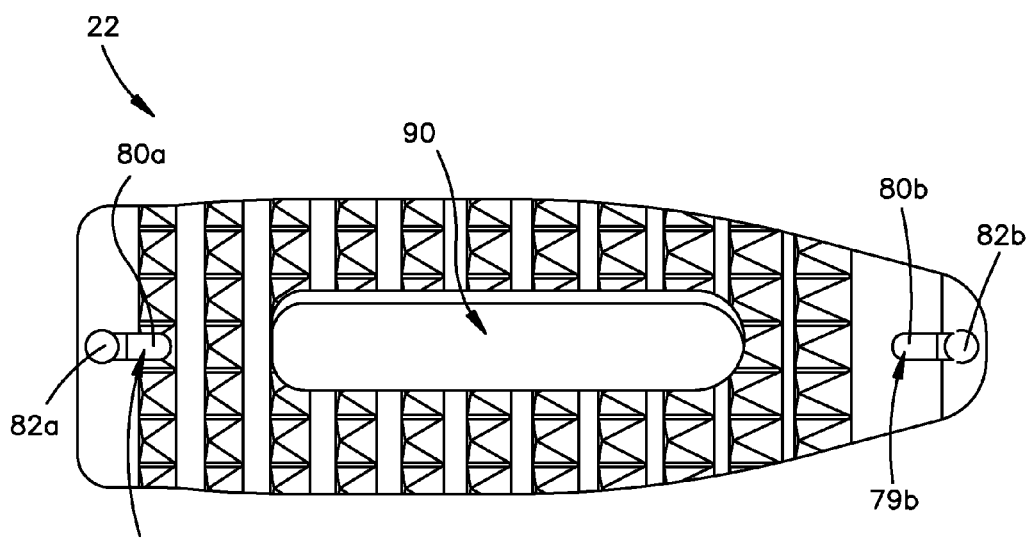
FIG. 2D is a top plan view of the intervertebral implant shown in FIG. 2A.

As shown in FIG. 2D, the first and second ends 70 and 74 of the first flexible end plate 36 can include first and second attachment members 79a and 79b such that the attachment members can be movably coupled to the core body 28 proximate to the posterior and anterior ends 40 and 44 of the core body 28. As shown, the first and second attachment members 79a and 79b can define first and second slots 80a and 80b, respectively, which are elongate along the first direction and are carried by the first and second ends 70 and 74, respectively. As shown in FIG. 2B, implant 22, or at least the core 26 of the implant, can include first and second fixation members 82a and 82b that extend through the first and second slots 80a and 80b and into the first outer surface 30 of the core body 28 to thereby couple the first flexible end plate 36 to the core body 28. The first flexible end plate 36 can be coupled to the core body 28 such that the first and second fixation members 82a and 82b limit the movement of the first and second ends 70 and 74 of the end plate 36 along the first direction when the flexible end plate 36 flexes toward the compressed configuration.

As shown in FIG. 2B, the first and second fixation members 82a and 82b can be pins that couple to the core body 28 through an interference fit. For example, the fixation members 82a and 82b can include a shaft 84 and a head 86 that extends out from an end of the shaft 84. The head 86 can be configured to have a dimension that is greater than that of a lateral dimension of the slots 80a and 80b and the shaft 84 can be configured to have a dimension that is less than the lateral dimension of the slots 80a and 80b. Therefore, the first and second ends 70 and 74 can be coupled to the core body 28 while at the same time be capable of translating along the first direction. It should be appreciated, however, that the fixation members 82a and 82b can have any configuration as desired. For example, the fixation members 82a and 82b can be threaded. Moreover, it should be appreciated that the first and second ends 70 and 74 can be coupled to the core body 28 with structure other than fixation members. For example, the core body 28 can define slots that are configured to translatably receive the first and second ends 70 and 74.

As shown in FIG. 2D, the first flexible end plate 36 can define a middle region 89 that extends from the first attachment member 79a to the second attachment member 79b. The first flexible end plate 36 can include at least one channel 90 that extends through the middle region 89 from the inner surface 62 to the bone facing surface 64 such that the at least one channel 60 of the core 26 and the at least one channel 90 of the flexible end plate 36 are substantially aligned along the second direction. The aligned channels 60 and 90 can help promote boney in-growth after the implant 22 has been inserted into the intervertebral space 18. Furthermore, the flexible end plate 36 can define a plurality of teeth 94 that extend out from the bone facing surface 64. The teeth 94 can be configured to prevent migration of the intervertebral implant 22 after the implant 22 has been inserted into the intervertebral space 18.

As the first and second ends slide along the core 26, an entirety of the middle region 89 can be spaced from the core 26 along the first direction. It should be appreciated, however, that in some embodiments, as the first and second ends slide along the core 26 portions of the middle region 89 can be in contact with the core 26. Moreover, it should be appreciated, that while the first and second attachment members 79a and 79b or at least the first and second ends 70 and 74 are illustrated as sliding along the first outer surface 30, the first and second attachment members 79a and 79b or at least the first and second ends 70 and 74 can slide along inner surfaces defined by the core 26.

With continued reference to FIGS. 2A-2F, the second flexible end plate 38 can be substantially identical to the first flexible end plate 36 and can include like structure unless otherwise described. It should be appreciated, however, that while in the illustrated embodiment the first and second flexible end plates 36 and 38 are substantially identical, the end plates 36 and 38 can include different structure and have different shapes as desired.

As shown in FIG. 2B, the second flexible end plate 38 defines an inner surface 162 and an opposed bone facing surface 164 that is configured to abut a vertebral body such as vertebral body 10b. As shown in FIG. 2C, the second flexible end plate 38 can be coupled to core 26 such that at least a portion of the inner surface 162 faces the second outer surface 34 and is spaced from the second outer surface 34 by a third distance $D_2$. The third distance $D_2$ can be a maximum distance that the inner surface 162 is spaced from the second outer surface 34 and can be taken at a longitudinal midline of the second flexible end plate 38 (e.g. halfway between first and second ends of the second flexible endplate 38). It should be appreciated, however, that the second distance $D_2$ can be taken at any point along the second flexible end plate 38, as desired.

As shown in FIG. 2C, the second flexible end plate 38 can define a first or posterior end 170 and a second or anterior end 174 that is spaced from the first end 170 along the first direction. The first and second ends 170 and 174 can be coupled to the core body 28 such that the second flexible end plate 38 is bowed along the first direction. The flexible end plate 38 is flexible between a first or initial configuration and a second or compressed configuration whereby the distance $D_2$ is decreased or the at least a portion of the inner surface 162 is spaced from the second outer surface 34 by a fourth distance that is less than the third distance. That is, the second flexible end plate 38 is configured to resiliently flex toward the compressed configuration such that as the flexible end plate flexes toward the compressed configuration, the first end 170 moves relative to the core 26 along the first direction and the portion of the inner surface 162 moves toward the second outer surface 34 such that the distance $D_2$ is decreased. Similarly, the second end 174 is configured to move relative to the core 26 along the first direction and away from the first end 170 when the second flexible end plate 38 flexes toward the compressed configuration. When in the initial configuration the third distance $D_2$ can be between about 0.5 mm and about 10.0 mm and when in the compressed configuration the fourth distance can be about 0.0 mm. It should be appreciated, however, that the third and fourth distances can be any number as desired when the second flexible end plate 38 is in the initial configuration or in the compressed configuration. Moreover, it should be appreciated, that while in the illustrated embodiment both the first and second ends 170 and 174 are configured to move along the first direction, in certain embodiments one of the first and second ends 170 and 174 can be fixed.

As shown in FIG. 2B, the first and second ends 170 and 174 of the second flexible end plate 38 can be moveably coupled to the core body 28 proximate to the posterior and anterior ends 40 and 44 of the core body 28. As shown, the second flexible end plate 38 can include first and second attachment members 179a and 179b such that the attachment members can be movably coupled to the core body 28 proximate to the posterior and anterior ends 40 and 44 of the core body 28. As shown, the first and second attachment members 179a and 179b can define first and second slots 180a and 180b that are elongate along the first direction and located proximate to the first and second ends 70 and 74, respectively. As shown in FIG. 2B, the core 26 can include third and fourth fixation members 182a and 182b that extend through the first and second slots 180a and 180b and into the second outer surface 34 of the core body 28 to thereby couple the second flexible end plate 38 to the core body 28 such that the third and fourth fixation members 182a and 182b limit the movement of the first and second ends 170 and 174 along the first direction when the flexible end plate 38 flexes toward the compressed configuration.

It should be appreciated that while the first flexible end plate 36 is coupled to the core body 28 with first and second fixation members 82a and 82b and the second end plate 38 is coupled to the core body 28 with third and fourth fixation members 182a and 182b, the first and second flexible end plates 36 and 38 can be coupled to the core body 28 using a first fixation member that extends through the core body 28 and through both first slots 80a and 180a, and a second fixation member that extends through the core body and through both second slots 80b and 180b.

The first and second flexible end plates 36 and 38 can be made from any bio-compatible material as desired. For example, the first and second flexible end plates 36 and 38 can be made from a bio-compatible metal such as Titanium, Steel, or any material that can provide spring-action. The first and second end plates 36 and 38 can also have a stiffness that is configured to support or otherwise match the stiffness of the vertebral bodies 10a and 10b. For example, the modulus of elasticity of cortical bone is between 7 and 30 GPa and the first and second endplates 36 and 38 can have a stiffness that is configured to support this range of moduli. Therefore, the first and second endplates 36 and 38 can have a stiffness that is between about 7 GPa and about 30 GPA. It should be appreciated, however, that the first and second end plates 36 and 38 can have any stiffness as desired. For example, the modulus of elasticity of cancellous bone is 55.6 MPa and the first and second end plates 36 and 38 can have a stiffness that is about 55.6 MPa to thereby match the stiffness of the cancellous bone in the rare case that the cortical bone is lost and the cancellous bone is exposed. It should be appreciated, that the stiffness of the end plates 36 and 38 can be dependent on a variety of factors such as the material choice and the geometry of the end plates 36 and 38.

The implant 22 can be sold individually or as a kit that includes the core 26, a plurality of flexible end plates 36 and 38, and a plurality of fixation members. At least one of the end plates 36 and 38 can have a stiffness that is different than the stiffness of at least one of the other flexible end plates. It should be appreciated, however, that some of the end plates of the plurality of end plates can have the same stiffness. Moreover, it should be appreciated, that the end plates of the plurality of end plates can have different shapes, be made from different materials, and/or have different coupling features.

Now in reference to FIGS. 3A-3F, an intervertebral implant 222 in accordance with another embodiment can include a first end plate 226, a second end plate 230 coupled to the first end plate 226, and a biasing member 234 coupled between the first and second end plates 226 and 230 along a first direction. The first end plate 226 is configured to move relative to the second end plate 230 along the first direction, such as along the transverse direction, between an initial or first configuration and a compressed or second configuration and movement of the first end plate from the first configuration to the second configuration causes the biasing member 234 to compress so as to bias the first end palate along the first direction from the second configuration toward the first configuration.

As shown in FIGS. 3A-3E, the first end plate 226 includes a first body 240 that is elongate along a second direction, such as along the longitudinal direction or insertion direction. The first body 240 defines a first bone facing surface 244 and a first inner or internal ceiling surface 248 that is spaced from the first bone facing surface 244 along a first direction, such as along the transverse direction. The first body 240 can define a first or posterior end 252 and a second or anterior end 256. The first end plate 226 can further include at least one wall that extends from the first body 240 substantially along the first direction. For example, the first end plate 226 can include a pair of side walls 260 that extend from the posterior end 252 to the anterior end 256. The side walls 260 can extend toward each other as the side walls 260 extend from the posterior end 252 toward the anterior end 256 so as to define a nose 258 at the anterior end 256. The side walls 260 can be spaced from each other along a third direction, such as along the lateral direction A, such that the posterior end 252, the anterior end 256, and the side walls 260 define a cavity 264 of the first body. Therefore, the at least one wall can be a single continuous wall that includes the posterior end 252, anterior end 256, and side walls 260 such that the cavity 264 is at least partially defined by the at least one wall and the internal ceiling surface 248.

In particular, the cavity 264 can be defined by a first pair of internal side surfaces 272 that are spaced along the second direction, and a second pair of internal side surfaces 276 that are spaced along the third direction. As shown, the internal side surfaces 272 of the first pair of side surfaces 272 are spaced from each other along the first direction by a distance $D_3$. The distance $D_3$ can be any dimension as desired so long as the cavity 264 can receive a portion of the second end plate 230.

Figure 3B:
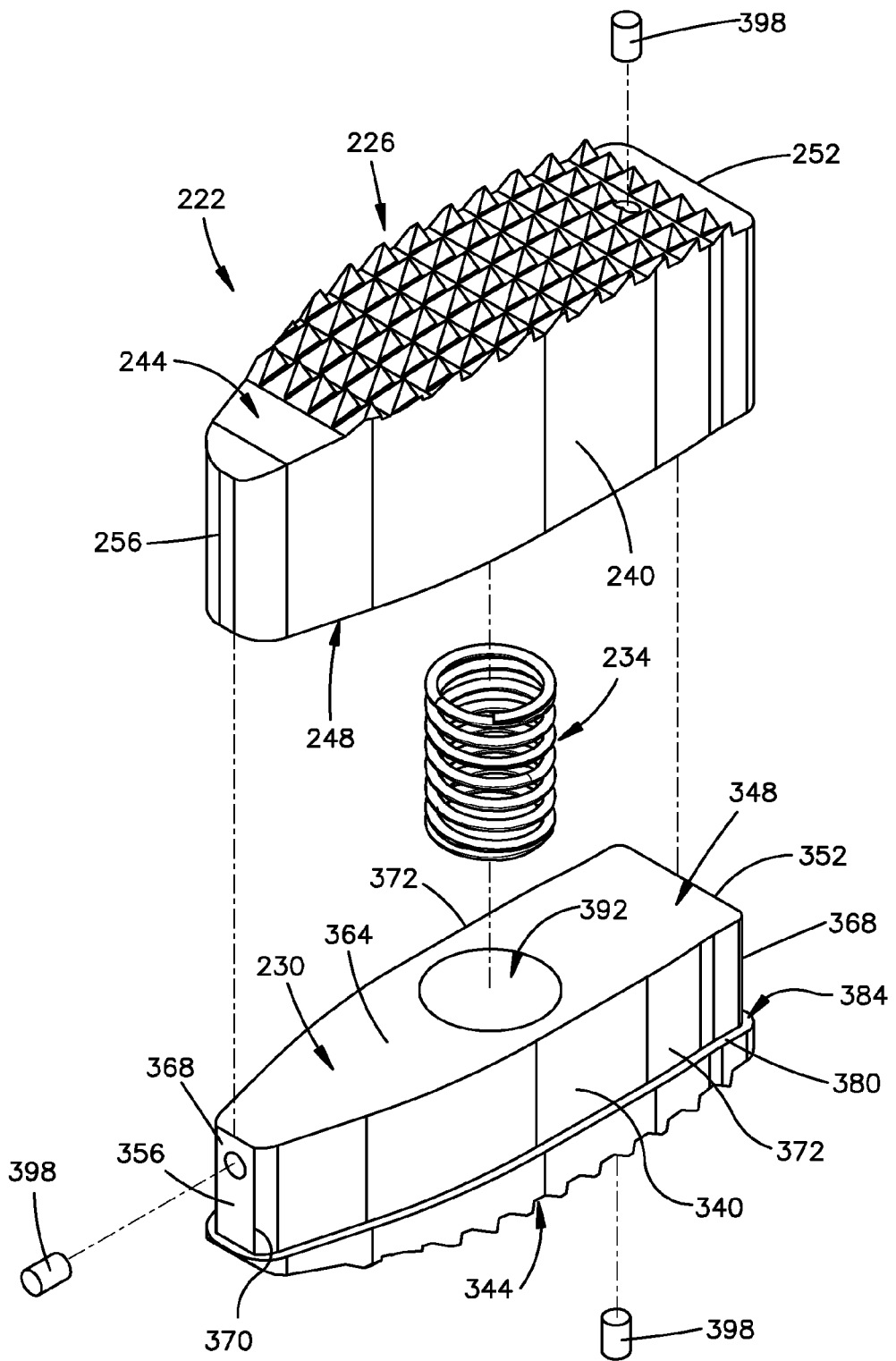
FIG. 3B is an exploded perspective view of the intervertebral implant shown in FIG. 3A.
Figure 3C:
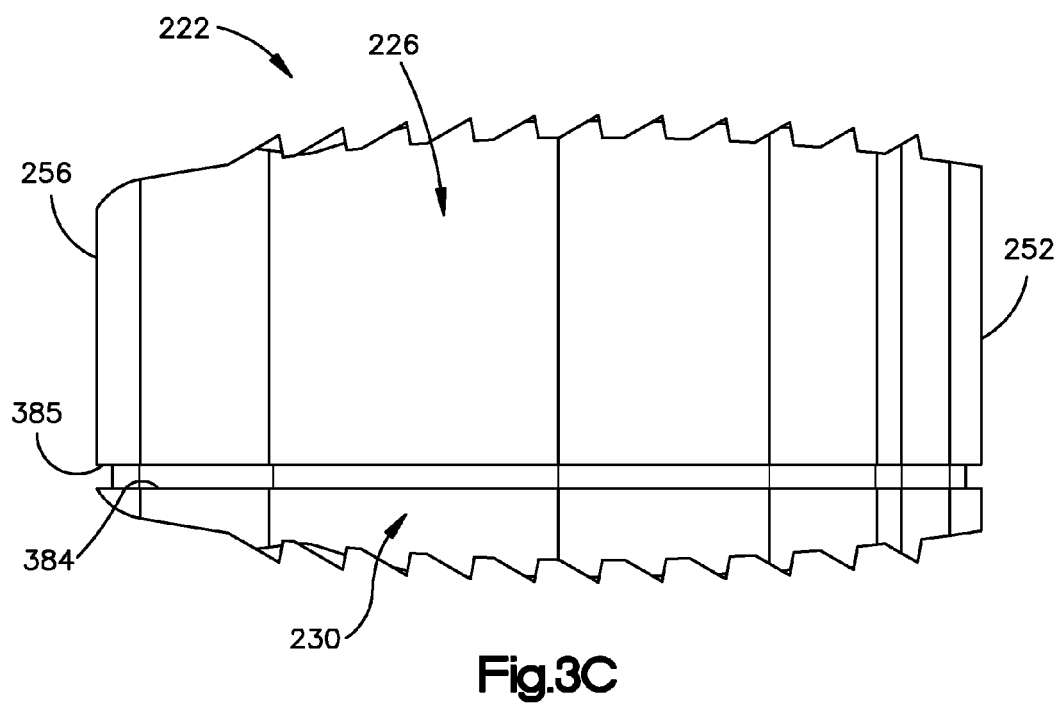
FIG. 3C is a side elevation view of the intervertebral implant shown in FIG. 3A.
Figure 3D:
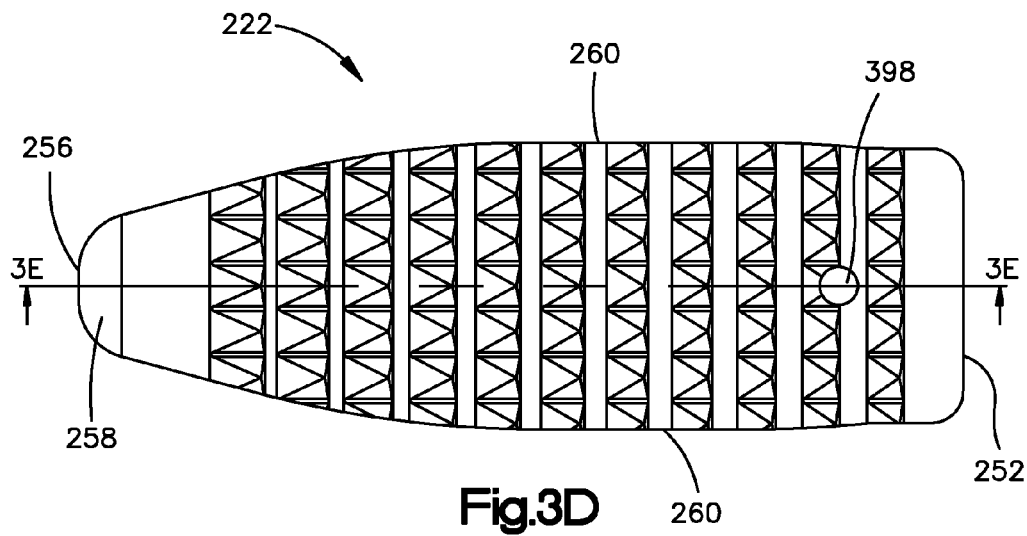
FIG. 3D is a top plan view of the intervertebral implant shown in FIG. 3A.
Figure 3E:
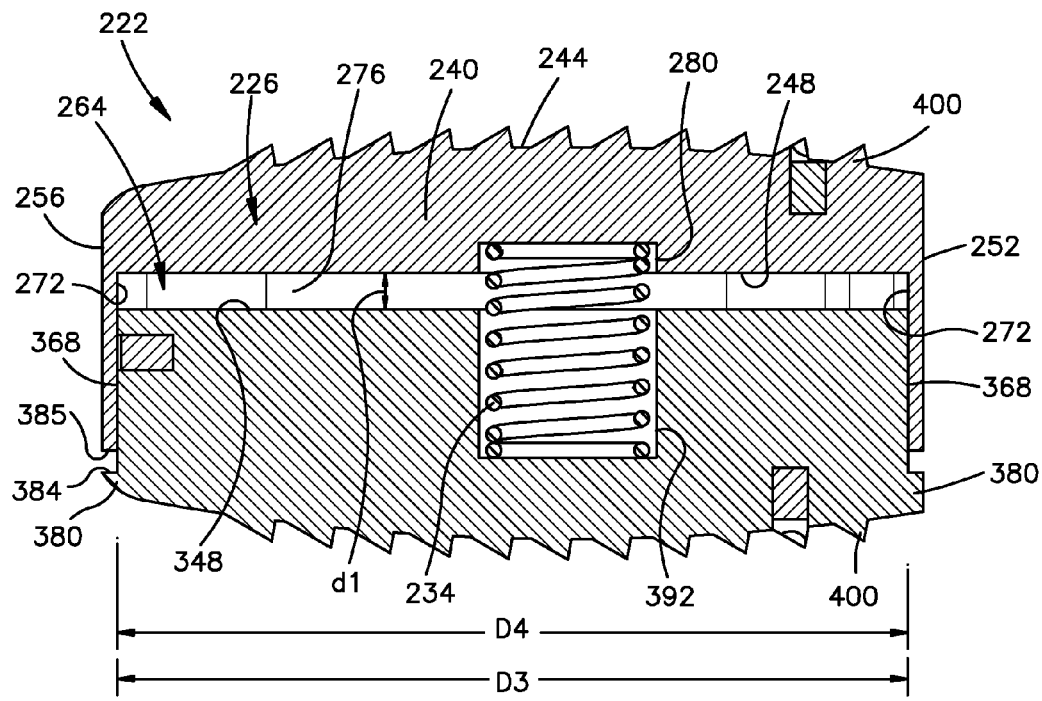
FIG. 3E is a cross-sectional view of the intervertebral implant shown in FIG. 3A taken through the line 3E-3E.
Figures 3F, 3G:
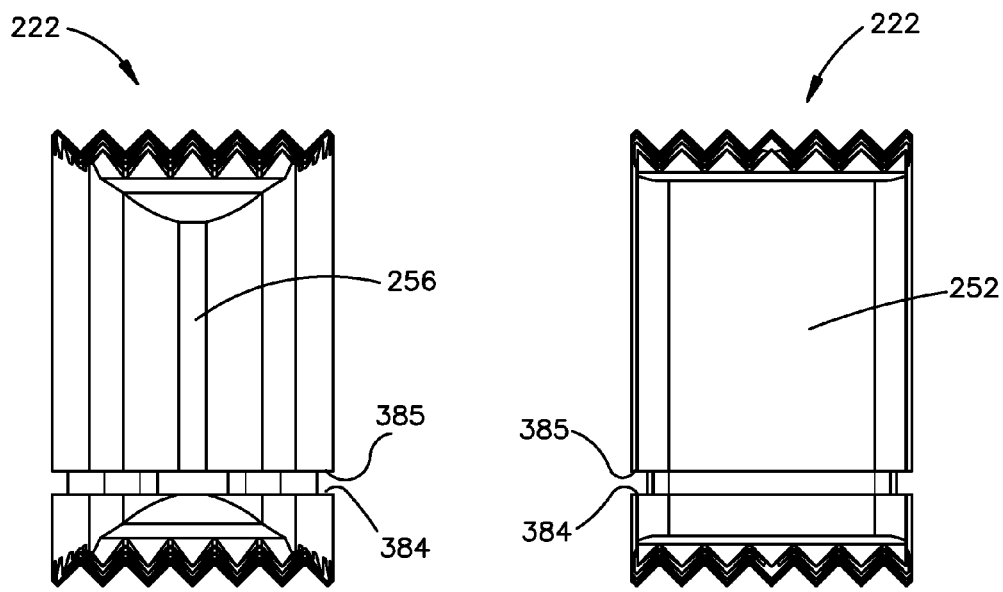
FIG. 3F is a front elevation view of the intervertebral implant shown in FIG. 3A.
FIG. 3G is a rear elevation view of the intervertebral implant shown in FIG. 3A.

As shown in FIG. 3E, the first end plate 226 further includes a recess 280 that extends into the internal ceiling surface 248 and toward the first bone facing surface 244. The recess 280 can be configured as a bore as illustrated and can be configured to receive a portion of the biasing member 234. It should be appreciated, however, that the recess 280 can have any configuration as desired. For example, the recess 280 can be substantially cubed shaped. Moreover, it should be appreciated, that the end plate 226 can include multiple recesses 280 if desired.

With continued reference to FIGS. 3A-3E, the second end plate 230 includes a second body 340 that is elongate along the second direction, such as along the longitudinal direction. As shown, the second body 340 defines a second bone facing surface 344 and a second inner surface 348 that is spaced from the second bone facing surface 344 along the first direction, such as along the transverse direction. The second body 340 can define a first or posterior end 352 and a second or anterior end 356 that is spaced form the posterior end 352 along the second direction. At least a portion of the second body 340 defines a core 364 that is configured to be received by the cavity 264 of the first body 240 such that the internal ceiling surface 248 faces the second inner surface 348. Therefore, the core 364 can be said to define the second inner surface 348.

The core 364 can define a first pair of external side surfaces 368 that are spaced along the second direction and a second pair of external side surfaces 372 that are spaced along the third direction. The second pair of side surfaces 372 extend toward each other as the side surfaces 372 extend from the posterior end 352 toward the anterior end 356 such that the core 364 defines a nose 370 at the anterior end 356. The external side surfaces 368 of the first pair of external side surfaces 368 are spaced from each other along the first direction by a distance $D_4$. The distance $D_4$ can be substantially equal to the distance $D_3$ such that the core 364 can be received within the cavity 264. It should be appreciated, however, that the distance $D_4$ can be any dimension as desired so long as the cavity 264 can receive the core 364 of the second end plate 230. Moreover, it should be appreciated that while in the illustrated embodiment the core 364 has shape that is substantially identical to that of the cavity 264, in certain embodiments the shapes of the core and the cavity can be different so long as the cavity can receive the core.

The anterior and posterior ends 252 and 256 can trap the core 364 within the cavity 264. Therefore, the anterior and posterior ends 252 and 256 can be said to be first and second attachment members. As the core 364 moves within the cavity 264, the first and second attachment members move or otherwise will slide along the core along the first direction.

As shown in FIGS. 3B and 3E, the second end plate 230 can further include a shoulder 380 that extends out from the second body 340 such that the shoulder 380 defines an abutment surface 384 that faces an end 385 of the at least one wall. The shoulder 380 can be configured to limit movement of the first end plate 226 relative to the second end plate 230 along the first direction when the end 385 abuts the abutment surface 384. The shoulder 380 can extend completely around the second body 340 and can be continuous as illustrated or the shoulder 380 can be segmented as desired. It should be appreciated, however, that in certain embodiments, the internal ceiling surface 248 can abut the second inner surface 348 to thereby limit the movement of the first end plate 226 relative to the second end plate 230 along the first direction.

As shown in FIG. 3E, the second end plate 230 further includes a recess 392 that extends into the second inner surface 348 and toward the second bone facing surface 344. The recess 392 can be configured as a bore as illustrated and can be configured to receive a portion of the biasing member 234. It should be appreciated, however, that the recess 392 can have any configuration as desired. For example, the recess 392 can be substantially cubed shaped. Moreover, it should be appreciated, that the second end plate can include any number of recesses 392 as desired.

The first and second end plates 226 and 230 can be made from any bio-compatible material such as PEEK and/or Titanium. Furthermore, at least one of the first end plate 226 and the second end plate 230 can include a radio-opaque marker 398 that is configured to indicate the position of the implant during implantation. In the illustrated embodiment, the first end plate 226 includes one marker 398 and the second end plate 230 includes two markers 398. It should be appreciated, however, that the first and second end plates 226 and 230 can include any number of markers 398 as desired, in any direction as desired, and of any shape (e.g. pin, ball, etc) as desired.

Furthermore, the first and second end plates 226 and 230 can define a plurality of teeth 400 that extend out from the bone facing surfaces 244 and 344. The teeth 400 can be configured to prevent migration of the intervertebral implant 222 after the implant 222 has been inserted into the intervertebral space 18. Moreover, it should be appreciated that the first and second endplates 226 and 230 can define channels and windows similar to those of the implant 22 to thereby further promote boney in-growth.

As shown in FIGS. 3B and 3E, the biasing member 234 can be positioned in the recesses 280 and 392 of the first and second end plates 226 and 230. Therefore, the recess 280 of the first end plate 226 can be coaxial with the recess 392 of the second end plate 230 when the core 364 is received by the cavity 264 such that the biasing member 234 is trapped within the recesses 280 and 392. The biasing member 234 can be a spring such as a circular compression spring as illustrated. It should be appreciated, however, that the biasing member 234 can have any configuration as desired. For example, the biasing member 234 can be configured as a solid compression member.

The biasing member 234 can have a stiffness that is configured to support or otherwise match the stiffness of the vertebral bodies 10a and 10b. For example, the modulus of elasticity of cortical bone is between 7 GPa and 30 GPa and the biasing member 234 can have a stiffness that is configured to support this range of moduli. Therefore, the biasing member 234 can have a stiffness that is between about 7 GPa and about 30 GPA. It should be appreciated, however, that the biasing member 234 can have any stiffness as desired. For example, the modulus of elasticity of cancellous bone is 55.6 MPa and the biasing member 234 can have a stiffness of about 55.6 MPa.

As shown in FIG. 3E, when the first end plate 226 is coupled to the second end plate 230 at least one of the first end plate 226 and the second end plate 230 is configured to move relative to the other along the first or transverse direction between an initial or first configuration and a compressed or second configuration. When in the initial configuration, the internal ceiling surface 248 is spaced from the second inner surface 348 along the first direction by a first distance $d_1$. When in the compressed configuration, the internal ceiling surface 248 is spaced from the second inner surface 348 along the second direction by a second distance $d_2$ that is less than the first distance $d_1$. Therefore, it can be said that when the first end plate 226 moves toward the compressed configuration, the first distance $d_1$ decreases. The first distance $d_1$ can between about 0.5 mm and about 10.0 mm and the second distance $d_2$ can be about 0 mm. It should be appreciated, however, that the first and second distances $d_1$ and $d_2$ can be any distances as desired.

When in the compressed configuration, the biasing member 234 is configured to bias the first end plate 226 toward the initial configuration. It should be appreciated, however, that the implant 222 can include more than one biasing member 234 as desired. For example, the implant 222 can include two biasing members that bias the first end plate 226 toward the initial configuration.

The first and second end plates 226 and 230 can be coupled together by the biasing member 234 or the at least one side wall can include fingers that engage the core so as to allow the core to move within the cavity along the first direction. It should be appreciated, however, that the first and second end plates 226 and 230 can be coupled together using any structure as desired so long as the core is capable of moving along the first direction within the cavity.

When the implant 22 or the implant 222 is inserted into the intervertebral space 18 the implants 22 and 222 can substantially match the stiffness of the vertebral bodies 10a and 10b to thereby promote fusion. Because of the construction of the implants 22 and 222, the implants 22 and 222 can be customized to match a variety of stiffnesses. Therefore, it can be said that in some embodiments the implants 22 and 222 are customizable or have adjustable stiffnesses. It should be appreciated, however, that the implants 22 and 222 can be constructed to have a specified stiffness.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:

1. An intervertebral implant comprising:
    a core defining a rear end and a front end that is spaced from the rear end along an insertion direction;
    an end plate that defines a bone facing surface having a plurality of teeth extending outwardly therefrom and an inner surface that is opposite the bone facing surface along a first direction, substantially perpendicular to the insertion direction, the end plate defining a first end including a first attachment member, and the end plate defining a second end that is spaced from the first end, the second end including a second attachment member that is spaced from the first attachment member, the first and second attachment members being movably coupled to the core such that at least a portion of the inner surface faces a surface of the core, such that the portion is spaced from the surface of the core a first distance along the first direction, and so as to bias the portion of the inner surface away from the surface of the core,
    wherein the end plate is resiliently movable toward the core along the first direction without causing movement of the core such that 1) the portion of the inner surface is spaced from the surface of the core a second distance along the first direction that is less than the first distance, and 2) at least one of the first and second ends is in contact with the surface of the core as the at least one of the first and second ends slides along the surface of the core.

2. The intervertebral implant of claim 1, wherein the first and second attachment members are spaced along a second direction that is substantially perpendicular to the first direction, and the at least one of the first and second attachment members moves along the core along the second direction.

3. The intervertebral implant of claim 2, wherein the second direction coincides with the insertion direction.

4. The intervertebral implant of claim 3, wherein the end plate is flexible so as to resiliently move toward the core along the first direction.

5. The intervertebral implant of claim 1, wherein the first and second ends carry the first and second attachment members, respectively, the core defines first and second outer surfaces, and at least one of the first and second ends is configured to slide along a respective one of the first and second outer surfaces.

6. The intervertebral implant of claim 5, wherein the endplate defines a middle region that extends from the first attachment member to the second attachment member, and the first and second ends slide along the core when an entirety of the middle region is spaced from the core along the first direction.

7. The intervertebral implant of claim 1, wherein the at least one of the first and second attachment members moves along the core along the first direction.

8. An intervertebral implant comprising:
    a core having a core body that defines first and second outer surfaces that are spaced from each other along a first direction, the core body being elongate along a second direction that is perpendicular to the first direction; and
    a flexible end plate that defines an inner surface and a bone facing surface that is spaced from the inner surface along the first direction, the flexible end plate being coupled to the core such that at least a portion of the inner surface faces the first outer surface and is spaced from the first outer surface by a first distance, the flexible end plate further defining a first end configured to couple to the core and a second end configured to couple to the core, the second end spaced from the first end along the second direction,
    wherein, when the first and second ends are coupled to the core, the flexible end plate is configured to resiliently flex toward the core such that, as the flexible end plate flexes, 1) the first end moves relative to the core along the second direction, 2) the second end moves relative to the core along the second direction and away from the first end, and 3) the portion of the inner surface moves toward the first outer surface such that the at least a portion of the inner surface is spaced from the first outer surface by a second distance that is less than the first distance.

9. The intervertebral implant of claim 8, wherein the flexible end plate defines first and second slots that are elongate along the second direction, the first slot is located proximate to the first end and the second slot is located proximate to the second end, and the core includes first and second fixation members that are supported by the core body and extend through the first and second slots, respectively, to thereby couple the flexible end plate to the core body such that the first and second fixation members limit the movement of the first and second ends along the second direction when the flexible end plate flexes toward the core.

10. The intervertebral implant of claim 9, wherein the first and second fixation members are pins that extend from the core body.

11. The intervertebral implant of claim 10, wherein the pins couple to the core body through an interference fit.

12. The intervertebral implant of claim 8, wherein the flexible end plate is a first flexible end plate and the intervertebral implant further comprises a second flexible end plate that is coupled to the core such that at least a portion of an inner surface of the second flexible end plate faces the second outer surface and is spaced from the second outer surface by a third distance.

13. The intervertebral implant of claim 12, wherein the second flexible end plate is configured to resiliently flex toward the core such that as the second flexible end plate flexes, a first end of the second flexible end plate moves relative to the core along the second direction and the portion of the inner surface of the second end plate moves toward the second outer surface such that the at least a portion of the inner surface of the second end plate is spaced from the second outer surface by a fourth distance that is less than the third distance.

14. The intervertebral implant of claim 8, wherein the flexible end plate is made of a bio-compatible metal.

15. The intervertebral implant of claim 8, wherein the flexible end plate has a stiffness that is between about 7 GPa and about 30 GPa.

16. The intervertebral implant of claim 8, wherein the core includes at least one window that extends through the core body along a third direction that is transverse to the first and second directions.

17. The intervertebral implant of claim 8, wherein the core includes at least one channel that extends through the core body along the first direction, and the flexible end plate defines at least one channel that extends through the flexible end plate from the inner surface to the bone facing surface such that the at least one channel of the core and the at least one channel of the flexible end plate are substantially aligned along the first direction.

18. The intervertebral implant of claim 8, wherein the first and second distances are measured at a location halfway between the first and second ends.

19. The intervertebral implant of claim 18, wherein the flexible end plate is configured to have an initial configuration that defines the first distance and a compressed configuration that defines the second distance, and the flexible end plate is configured to flex between the initial configuration and the compressed configuration.

20. The intervertebral implant of claim 19, wherein the second distance is about 0 mm when the flexible end plate is in the compressed configuration.

21. The intervertebral implant of claim 20, wherein the flexible end plate is bowed along the second direction when in the initial configuration.

22. The intervertebral implant of claim 19, wherein the first distance is between about 0.5 mm and about 10.0 mm when the flexible end plate is in the initial configuration.

23. The intervertebral implant of claim 8, wherein the flexible end plate defines a plurality of teeth that extend out from the bone facing surface.

24. A kit comprising:
a core having a core body that is elongate along a first direction, defines a rear end and a front end that is spaced from the rear end along the first direction, and defines a pair of outer surfaces that are spaced from each other along a second direction that is perpendicular to the first direction; and
a plurality of flexible end plates, each flexible end plate defining an inner surface and an opposed bone facing surface, each flexible end plate being configured to attach to the core at a first attachment and a second attachment spaced from the first attachment along the first direction such that each flexible end plate is bowed along the first direction and at least a portion of the inner surface of each flexible end plate faces one of the outer surfaces, such that the first and second attachments limit movement of the flexible end plates along the first direction both towards and away from the front end of the core, and so as to bias at least a portion of the flexible end plates away from the core along the first direction.

25. The kit of claim 24, wherein each flexible end plate defines a first end and a second end that is spaced from the first end along the first direction, and each flexible end plate that is coupled to the core is configured to resiliently flex toward a compressed configuration such that as the flexible end plates flex toward the compressed configuration, the first and second ends of the flexible end plates move away from each other relative to the core and along the first direction.

26. The kit of claim 24 further comprising a plurality of pins that are configured to couple the flexible end plates to the core.

27. The kit of claim 24, wherein at least one of the flexible end plates has a stiffness that is different than the stiffness of at least one of the other flexible end plates.

28. The kit of claim 24, wherein at least one of the flexible end plates defines a plurality of teeth that extend out from the bone facing surface.

* * * * *